(12) United States Patent
Shin

(10) Patent No.: US 11,224,368 B2
(45) Date of Patent: Jan. 18, 2022

(54) KIT FOR SEPARATING AND CONCENTRATING BODY FLUID CELLS

(71) Applicant: Rev-Med, Inc., Seongnam-si (KR)

(72) Inventor: Bong Geun Shin, Suwon-si (KR)

(73) Assignee: REV-MED, INC., Seongnam-si (KR)

( * ) Notice: Subject to any disclaimer, the term of this patent is extended or adjusted under 35 U.S.C. 154(b) by 240 days.

(21) Appl. No.: 16/686,883

(22) Filed: Nov. 18, 2019

(65) Prior Publication Data

US 2020/0170558 A1   Jun. 4, 2020

(30) Foreign Application Priority Data

Nov. 30, 2018   (KR) .......................... 10-2018-0152046

(51) Int. Cl.
*A61B 5/15* (2006.01)
*C12N 5/078* (2010.01)

(52) U.S. Cl.
CPC .. *A61B 5/150755* (2013.01); *A61B 5/150351* (2013.01); *A61B 5/150534* (2013.01); *C12N 5/0634* (2013.01)

(58) Field of Classification Search
CPC ....... A61B 5/150351; A61B 5/150755; A61M 1/029; B01L 2300/0832; B01L 3/5021; C12M 47/04; G01N 33/491
See application file for complete search history.

(56) References Cited

FOREIGN PATENT DOCUMENTS

| KR | 20130119773 A | * | 11/2013 | |
|---|---|---|---|---|
| KR | 20140069871 A | * | 6/2014 | |
| WO | WO-2015025912 A1 | * | 2/2015 | ............ A61M 1/029 |

OTHER PUBLICATIONS

Shin Bong Geun—KR-20130119773-A machine translation (Year: 2013).*
Kim Sang Hyun—KR-20140069871-A machine translation (Year: 2014).*
Kaneda Kenta—WO-2015025912-A1 machine translation (Year: 2015).*

* cited by examiner

*Primary Examiner* — Bradley R Spies
(74) *Attorney, Agent, or Firm* — Knobbe Martens Olson & Bear LLP

(57) ABSTRACT

A kit for separating and concentrating body fluid cells is provided. The kit includes a first sealing cap provided with a first close contact body; a first cap connection housing having a first inner connection body in which a first elastic body having a first slit line formed at an end thereof, with which the first close contact body comes into elastic contact when coupled to the first sealing cap, is inserted and disposed in an inner hole so that the first inner connection body is assembled with the first sealing cap; a first housing having one end screw-coupled to the first cap connection housing, and having an inner partition wall formed therein so that a first connection hole corresponding to the inner hole is formed through the inner partition wall; a central housing having one end screw-coupled to the other end of the first housing.

15 Claims, 15 Drawing Sheets

KIT FOR SEPARATING AND CONCENTRATING BODY FLUID CELLS

CROSS-REFERENCE TO RELATED APPLICATION

This application claims priority to and the benefit of Korean Patent Application No. 2018-0152046 filed Nov. 30, 2018, the disclosure of which is incorporated herein by reference in its entirety.

BACKGROUND

1. Field

The present disclosure relates to a kit for separating and concentrating body fluid cells, which includes stem cells.

2. Discussion of Related Art

In general, plasma is a neutral pale yellow liquid component obtained by separating and removing blood cells from bone marrow or blood, contains platelets, growth factors, proteins, sugars, lipids, inorganic salts, and metabolites as well as water, and serves to maintain constant osmotic pressure and hydrogen ions in the cells.

Based on these medical grounds, there are known autologous platelet-rich plasma regeneration therapies, that is, a platelet-rich plasma therapy and an autologous bone marrow therapy, in which bone marrow or blood is collected from a patient to separate platelets using a centrifuge, and the platelets are applied on a wound or injected into a tendon/cartilage.

Here, platelet-rich plasma (PRP) obtained by centrifuging bone marrow or blood refers to a highly enriched plasma component which is richer in platelets compared to normal bone marrow or blood. Therefore, the platelet-rich plasma (PRP) contains various growth factors, and thus may serve to heal wounds and regenerate and reconstruct injured areas.

For example, platelet-rich plasma (PRP) is injected into an injured area in a tendon, cartilage, and the like to reconstruct the injured area, and have advantages in that it has no side effects and a quick therapeutic effect because an autonomous body fluid such as stem cells, bone marrow, or blood is used.

Patent Document 1: KR10-1170028 B1 discloses the related technology.

The disclosure of this section is to provide background information relating to the invention. Applicant does not admit that any information contained in this section constitutes prior art.

SUMMARY

Aspects of the invention provide a kit for separating and concentrating body fluid cells capable of basically preventing the inflow of external air during injection of a body fluid such as blood or bone marrow collected using a syringe or during extraction of a centrifugate after centrifugation to basically prevent contamination of the centrifugate due to contact with air and preventing the incorporation of foreign substances included in the body fluid during blood collection. Aspects of the invention also provides a kit for separating and concentrating body fluid cells capable of prevention of contamination of a body fluid that is a centrifugate such as blood or bone marrow by basically preventing the inflow of external air and the contact with air while the collected centrifugate is injected into a syringe during a procedure of sequentially separating body fluid (e.g., blood or bone marrow) using the specific gravity difference after centrifugation of the body fluid.

According to an aspect of the present invention, there is provided a kit for separating and concentrating body fluid cells, which includes a first sealing cap provided with a first close contact body in an assembly hole formed through a body; a first cap connection housing having a first inner connection body in which a first elastic body having a first slit line formed at an end thereof, with which the first close contact body comes into elastic contact when coupled to the first sealing cap, is inserted and disposed in an inner hole so that the first inner connection body is assembled with the first sealing cap; a first housing having one end screw-coupled to the first cap connection housing and having an inner partition wall formed therein so that a first connection hole corresponding to the inner hole is formed through the inner partition wall; a central housing having one end screw-coupled to the other end of the first housing so that the one end of the central housing and the other end of the first housing are movable relative to each other by a screw and having a central partition wall, through which at least one communication hole is formed, formed therein to be filled with a body fluid; a second housing having one end screw-coupled to the other end of the central housing so that the one end of the second housing and the other end of the central housing are movable relative to each other by a screw and having a second connection hole, which corresponds to the first connection hole, formed therein; a second cap connection housing having a hollow support extending vertically from an inner surface thereof, which corresponds to the second connection hole, a filtering sieve for filtering a body fluid injected through a through hole formed in the hollow support, and a second inner connection body in which a second elastic body is inserted and disposed in an inner hole corresponding to the through hole so that the second cap connection housing is screw-coupled to the other end of the second housing; a second sealing cap having a second close contact body coming into elastic contact with an end of the second elastic body having a second slit line formed therein when coupled to the second cap connection housing so that the second close contact body is coupled to the second inner connection body; and a control unit having a first locking bar extending from the central partition wall toward the first connection hole, and a second locking bar extending from the central partition wall toward the second connection hole to selectively block or open the first connection hole or the second connection hole during mutual movement between the first and second housings and the central housing.

Preferably, the first close contact body or the second close contact body may include an extension bar having a predetermined length, which is inserted through an assembly hole of the first sealing cap or an assembly hole of the second sealing cap and has a close contact plate provided at an end thereof to cover the first slit line or the second slit line, wherein the close contact plate comes into elastic contact with the first elastic body or the second elastic body.

More preferably, the extension bar may include a ring-shaped protruding stage coming into contact with an outer rim of the assembly hole of the first sealing cap or the assembly hole of the second sealing cap.

Preferably, the first inner connection body may include a coupled portion coupled to a coupling portion extending from an outer rim of the assembly hole formed in the first sealing cap, and a connected portion integrally connected to a connecting portion extending from an outer rim of the central hole formed in the inner partition wall of the first cap connection housing.

More preferably, the first inner connection body may be provided as a stand-alone structure whose portion with which the connecting portion of the first cap connection housing comes into contact is coupled to the connected portion by means of any one of ultrasonic welding, screw coupling, and bonding methods.

More preferably, the connecting portion of the first cap connection housing may include a ring-shaped anchoring groove coming into contact with the connected portion of the first inner connection body.

More preferably, the first inner connection body may be provided as an integral structure extending from the connecting portion formed on the inner partition wall of the first cap connection housing.

Preferably, the second inner connection body may include a coupled portion coupled to a coupling portion extending from an outer rim of the assembly hole formed in the second sealing cap, and a connected portion integrally connected to a connecting portion extending from an outer rim of the through hole formed in the hollow support.

More preferably, the second inner connection body may be provided as a stand-alone structure whose portion with which the connecting portion of the hollow support comes into contact is coupled to the connected portion by means of any one of ultrasonic welding, screw coupling, and bonding methods.

More preferably, the connecting portion of the hollow support may include a ring-shaped anchoring groove coming into contact with the connected portion of the second inner connection body.

More preferably, the second inner connection body may be provided as an integral structure extending from the connecting portion formed at the hollow support.

Preferably, the first and second locking bars may include first and second insertion bars inserted into the first and second connection holes so that ends of the first and second insertion bars correspond, respectively, to the first and second connection holes, and first and second fixing bars assembled to correspond to fixing hole of a locking holder portion formed at the central partition wall, respectively.

More preferably, the first and second locking bars may include ring-shaped first and second protruding stages formed at boundary regions between the first and second insertion bars and first and second fixing bars, respectively, to be in contact with and caught in the fixing hole of the locking holder portion.

More preferably, the first and second fixing bars may include a pair of planar portions whose bodies are partially cut off to face each other in order to be joined in the same cross-sectional shape as a cross-sectional shape of the fixing hole while being assembled to correspond respectively to the fixing hole of the locking holder portion to overlap each other.

More preferably, one lateral planar portion of the pair of planar portions may include a plurality of latching portions formed to protrude at predetermined intervals, and the other planar portion may include a plurality of latched portions latched with the latching portions to generate a latching force.

BRIEF DESCRIPTION OF THE DRAWINGS

The above and other aspects, features and advantages of the present invention will become more apparent to those of ordinary skill in the art by describing in detail embodiments thereof with reference to the attached drawings, in which.

DETAILED DESCRIPTION OF EMBODIMENTS

Figure 1:
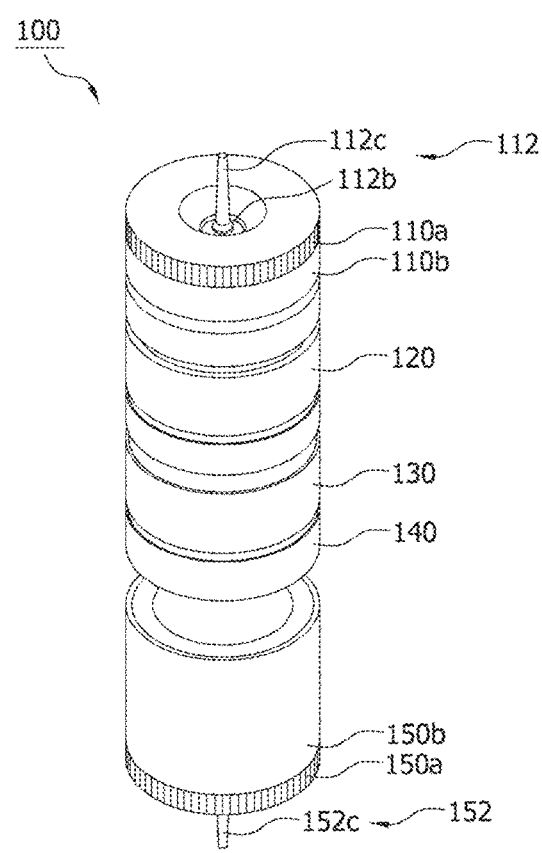
FIG. 1 is an overall perspective view showing a kit for separating and concentrating body fluid cells according to an embodiment of the present invention.

Hereinafter, embodiments of the present invention that may be easily practiced by a person having ordinary skill in the art will be described in detail with reference to the accompanying drawings. However, in describing a structural principle of the embodiments of the present invention in detail, detailed descriptions with respect to known functions or constructions will be omitted when the detailed descriptions are considered to make the gist of the present invention unclear.

Also, like numbers refer to like elements throughout the description of the figures.

Throughout the specification, a certain part being "connected" to another part means that the certain part is "directly connected" to the other part or that the certain part is "indirectly connected" to the other part through another member interposed between the two parts. Also, a certain part "including" a certain element signifies that the certain part may further include, instead of excluding, another element unless particularly indicated otherwise.

One example provides a separation apparatus capable of centrifuging an extract such as collected blood twice without exposing the extract to the air. However, to separate enriched platelets using this apparatus for separating blood, the separation of the enriched platelets should be performed in a state in which an opening formed in an outer surface of a kit is completely opened during a procedure of injecting the collected blood from a syringe into the kit. Due to this, because a large amount of air is allowed to flow through the completely opened opening while injecting blood, the blood serving as the centrifugate may be contaminated due to the contact of the blood with air.

Also, because the opened opening should be sealed as a separate sealing port to be separable after the blood injection, this results in inconvenience in use.

In addition, to seal the opened opening as the separate sealing port to be separable after the blood injection, this sealing involves a banding operation of banding and fixing an outer circumferential surface of a kit using a band having a sealant for sealing the opening, which is very troublesome. Also, because the banded and fixed band is disassembled from the kit in a centrifuge, it may allow blood in the kit to flow out during the centrifugation.

Also, to smoothly release the centrifuged components in the kit from the kit after the primary and secondary centrifugations, the banded and fixed band should be loosened to completely open the opening in order to convert a vacuum atmosphere in the kit into an atmospheric pressure state. As a result, contamination of the centrifuged components may be caused due to the inflow of a large amount of air through the completely opened opening, which acts as a main cause of reducing the reliability of the collected and separated components.

Further, in the case of the centrifugate such as bone marrow, foreign substances such as bone fragments included in the bone marrow are injected into the kit during a collection procedure, resulting in degraded centrifugation efficiency.

Figure 2:
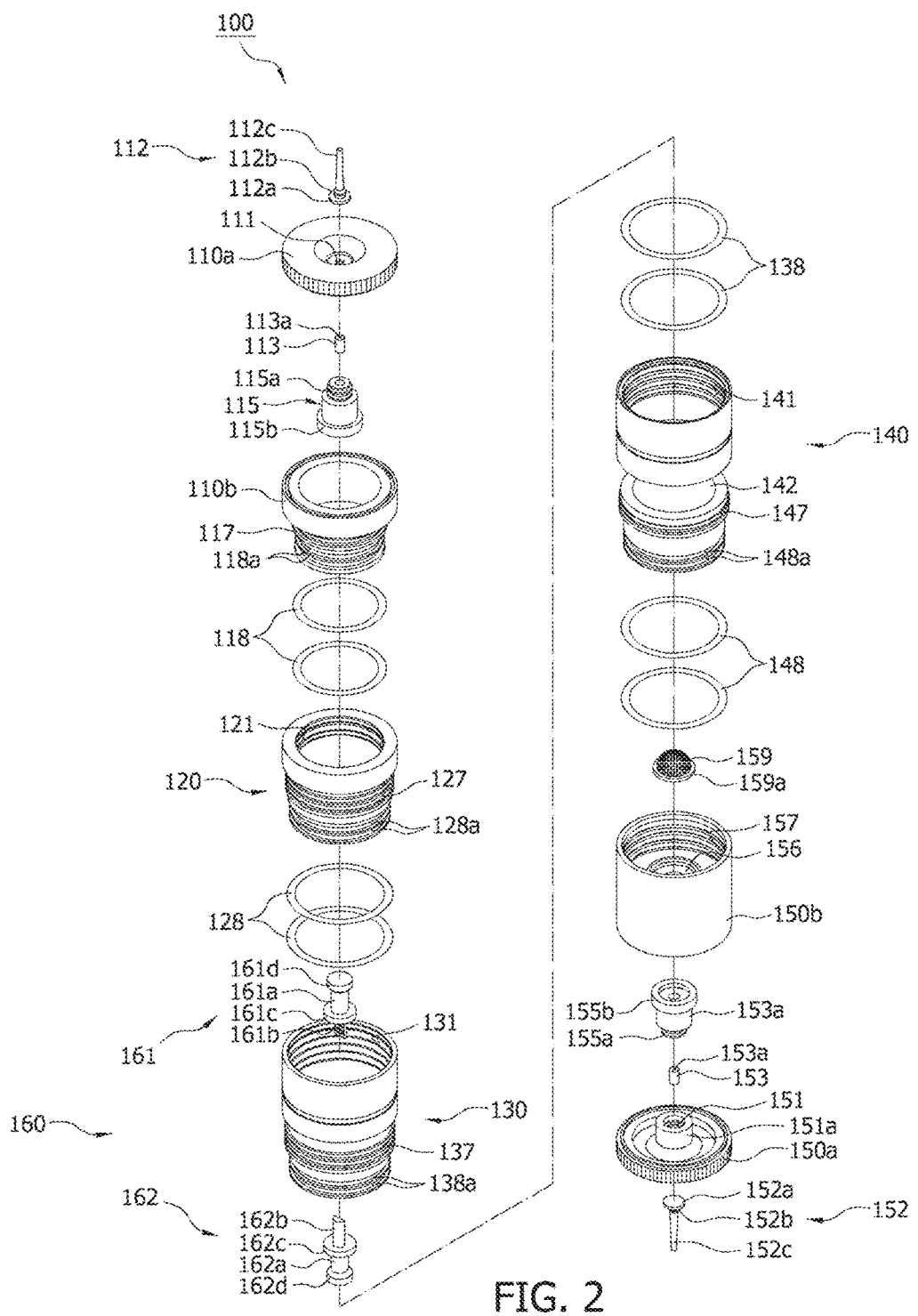
FIG. 2 is an exploded perspective view showing the kit for separating and concentrating body fluid cells according to an embodiment of the present invention.
Figure 3:
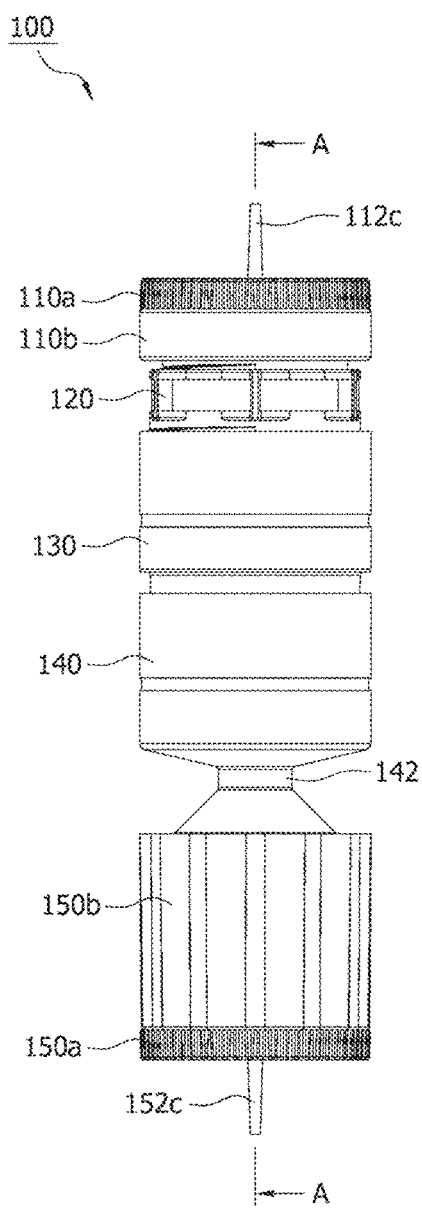
FIG. 3 is an exterior view showing the kit for separating and concentrating body fluid cells according to an embodiment of the present invention.
Figure 4A:
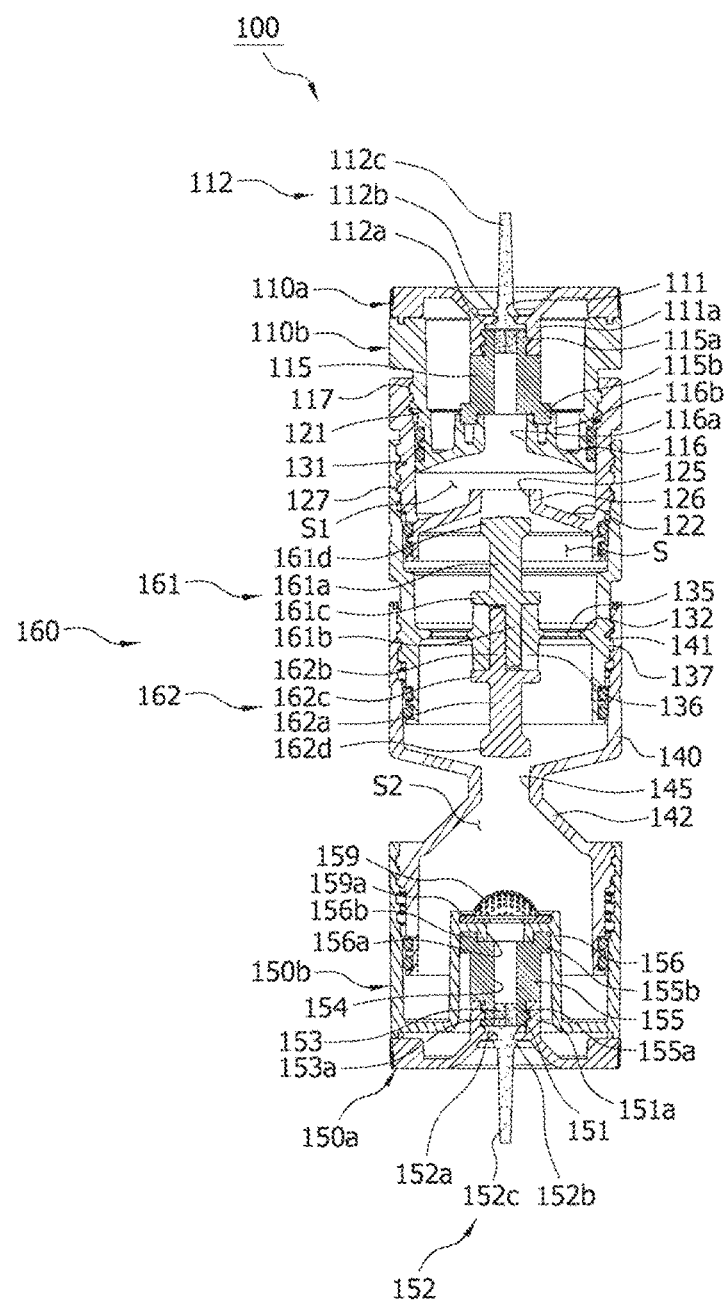
FIG. 4A is a longitudinal cross-sectional view taken along line A-A of FIG. 3.
Figure 4B:
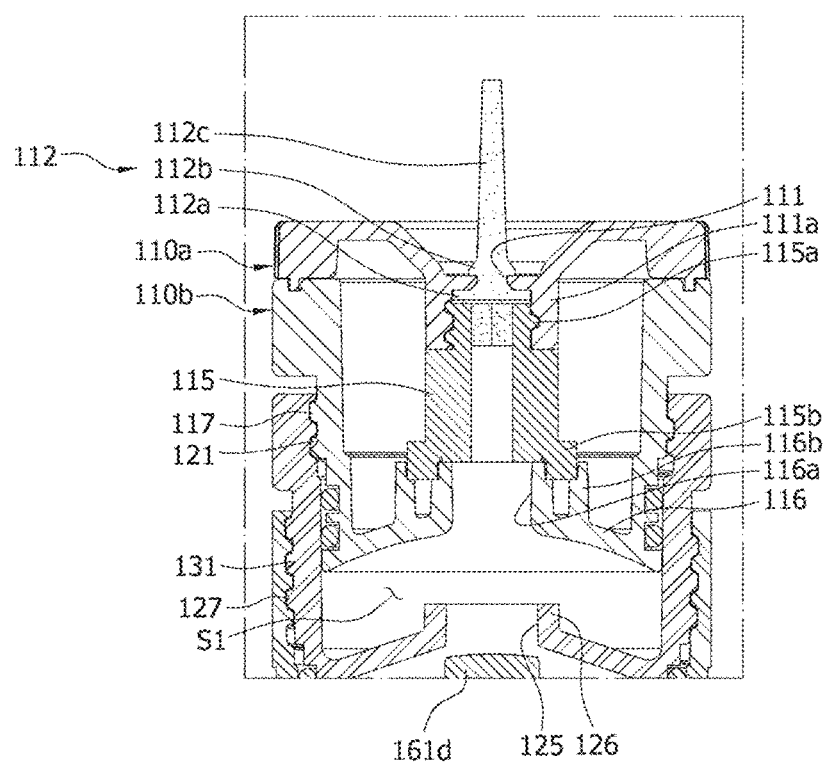
FIG. 4B is a detailed cross-sectional view showing the coupling between a first sealing cap and a first cap connection housing in the kit for separating and concentrating body fluid cells according to an embodiment of the present invention.
Figure 4C:
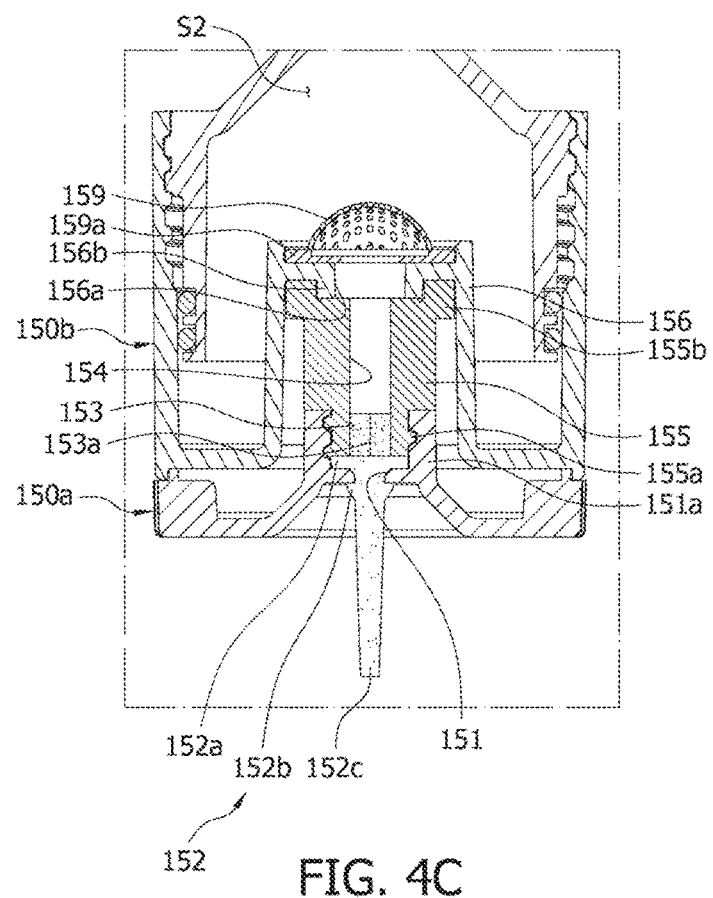
FIG. 4C is a detailed cross-sectional view showing the coupling between a second sealing cap and a second cap connection housing in the kit for separating and concentrating body fluid cells according to an embodiment of the present invention.

As shown in FIGS. 1 to 3, in embodiments, a kit 100 for separating and concentrating body fluid cells according to an embodiment of the present invention may include first and second sealing caps 110a, 150a, first and second cap connection housings 110b, 150b, first and second housings 120, 140, a central housing 130 and a control unit 160 in order to separate components included in a body fluid such as bone marrow or blood into multiple layers due to the specific gravity difference while sequentially performing primary and secondary centrifugation processes on the body fluid using a centrifuge, and finally optionally select any one of the separated components.

As shown in FIGS. 1, 2, 3, 4A and 4B, the first sealing cap 110a is a roughly disk-shaped, cover-type finishing member which is detachably coupled to the first cap connection housing 110b as a first close contact body 112 is assembled to correspond to a roughly circular assembly hole 111 formed through the center of the body.

The assembly hole 111 may be formed through a bottom surface of a concave groove recessed to a predetermined depth from the center of an outer surface (i.e., a top surface in the drawing) of the first sealing cap.

Such an inner surface (i.e., a bottom surface in the drawing) of the first sealing cap 110a includes a coupling portion 111a extending a predetermined length from an outer rim of the assembly hole 111 and having a female screw portion formed at an inner circumferential surface thereof.

As shown in FIGS. 1, 2, 3, 4A, and 4B, the first cap connection housing 110b may include a first inner connection body 115 having a first elastic body 113 with which an end of the first close contact body 112 comes into elastic contact when coupled to the first sealing cap 110a, and thus may be provided as a hollow cylindrical member that is detachably assembled with the first sealing cap 110a by means of the first inner connection body 115 integrally provided with or coupled to the first cap connection housing.

Such an outer bottom surface of the first cap connection housing 110b includes male screw portion 117 screw-coupled to the female screw portion formed at an inner top surface of the first housing.

The first elastic body 113 has a roughly cylindrical structure in which a straight or cruciform first slit line 113a is cut in a longitudinal direction along the center of the body so that the first slit line 113a is inserted into and disposed in an inner hole 114 formed through the first inner connection body.

Figure 5:
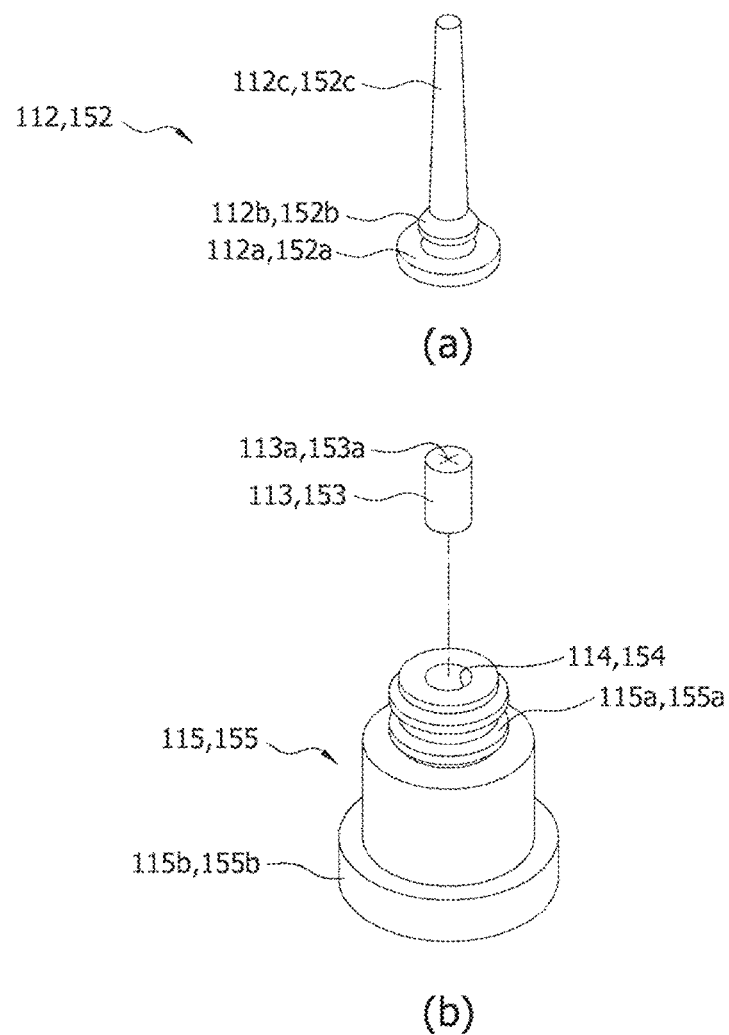
FIG. 5 shows perspective views which include (a) a perspective view showing first and second close contact bodies applied to the kit for separating and concentrating body fluid cells according to an embodiment of the present invention, and (b) a perspective view showing first and second elastic bodies and first and second inner connection bodies applied to the kit for separating and concentrating body fluid cells according to an embodiment of the present invention.

Here, as shown in FIG. 5A, the first close contact body 112 may include an extension bar 112c having a predetermined length, which is inserted through the assembly hole 111, has a roughly disk-shaped close contact plate 112a provided at an end thereof to cover the first slit line, and is gripped by a user, wherein the close contact plate 112a comes into elastic contact with the first elastic body. Also, the extension bar 112c may include a ring-shaped protruding stage 112b coming into contact with an outer rim of the assembly hole.

As shown in FIG. 5B, the first inner connection body 115 may include a coupled portion 115a having a male screw portion formed at an outer surface of one end thereof so that the male screw portion is coupled to a female screw portion of the coupling portion 111a extending a predetermined length from the outer rim of the assembly hole 111 formed in the first sealing cap 110a, and may also include a connected portion 115b formed at an outer surface of the other end thereof so that the connected portion 115b is integrally connected to a connecting portion 116b extending perpendicularly a predetermined length from an outer rim of a central hole 116a of an inner partition wall 116 extending from an inner surface of the first cap connection housing 110b.

In this case, the coupling between the coupled portion 115a of the first inner connection body 115 and the coupling portion 111a of the first sealing cap 110a is shown and described as the coupled portion 115a and the coupling portion 111a being detachably assembled by a screw-coupling method, but the present invention is not limited thereto. For example, the coupled portion 115a and the coupling portion 111a may be detachably assembled by other coupling methods.

Also, the connected portion 115b of the first inner connection body 115 may be integrally provided with the first cap connection housing by an ultrasonic welding method using welding heat of ultrasonic waves intensively applied to a contact site in a state in which the connected portion 115b is put on the connecting portion 116b formed at an inner partition wall of the first cap connection housing 110b so that the connected portion 115b comes into contact with the connecting portion 116b, but the present invention is not limited thereto. For example, the connected portion and the connecting portion may be coupled to each other by a screw coupling method or a bonding method.

In this case, the connecting portion 116b of the first cap connection housing 110b, with which the connected portion 115b of the first inner connection body 115 comes into contact in a state in which the connected portion 115b is put on the connecting portion 116b, may include a ring-shaped anchoring groove to increase a contact area with inner and outer rims of the connected portion 115b and stably and uniformly come into contact with the inner and outer rims of the connected portion 115b.

Also, when the connected portion 115b of the first inner connection body 115 is provided as a stand-alone structure which is coupled to the connecting portion formed at the inner partition wall of the first cap connection housing by means of any one of ultrasonic welding, screw coupling, and bonding methods, a primary assembly process of inserting the first elastic body 113 into the inner hole 114 of the first inner connection body 115 having a stand-alone structure is first performed, and a secondary assembly process of integrally coupling the first inner connection body to a connected portion of the first cap connection housing is then performed.

On the other hand, when the first inner connection body 115 is provided as an integral structure extending from the connecting portion 116b formed at the inner partition wall of the first cap connection housing, the number of component parts may be reduced by excluding an assembly process of integrally connecting the connecting portion of the first inner connection body and the connected portion of the first cap connection housing to each other.

Accordingly, when the first sealing cap 110a having the first close contact body is coupled to the first cap connection housing 110b by means of the first inner connection body having a first slit line formed therein, the first close contact body 112 composed of a soft elastic material such as a rubber material comes into elastic contact with the cut first slit line 113a to seal the first slit line 113a, thereby safely preventing the contents from flowing out through the first slit line during centrifugation. On the other hand, the first slit line of the first inner connection body is exposed to air during separation of the first sealing cap to forcibly insert an inlet of a syringe through the exposed first slit line, thereby forming a connection channel through which a collected body fluid is safely injected or centrifuged components are extracted therefrom without any contact with external air.

As shown in FIGS. 1, 2, 3, 4A and 4B, the first housing 120 may include a hollow cylindrical member which is detachably assembled with the first cap connection housing by forming a female screw portion 121, which is screw-coupled to the male screw portion 117 formed on an outer bottom surface of the first cap connection housing, on an outer surface of one end (i.e., an upper end) of the first housing 120.

Such a first housing 120 has an inner partition wall 122 having a first connection hole 125 formed through the center of the body, and the inner partition wall may include a roughly disk-shaped plate extending from an inner surface of the first housing in a radial direction.

The first connection hole 125 is preferably formed in a hollow cylindrical body 126 extending a predetermined length from the center of the inner partition wall toward the first sealing cap.

In this case, the hollow cylindrical body 126 having the first connection hole 125 formed therein may be formed at the apex of an inner partition wall with a conical cross-sectional shape having an outside diameter gradually tapered toward the first cap connection housing.

At least one O-ring member 118 for sealing a coupling site between an inner surface of the first housing 120 and an outer surface of the first cap connection housing 110b by being interposed therebetween is provided. Such an O-ring member may be selectively disposed in a ring-shaped ring groove 118a recessed from the inner surface of the first housing 120 or the outer surface of the first cap connection housing 110b.

An open outer surface of the other end of the first housing 120 includes another male screw portion 127 formed to be screw-coupled to the central housing 130.

Accordingly, the first cap connection housing 110b and the first housing 120 are assembled with each other by a screw-coupling method, when a connection channel is blocked by inserting a first locking bar provided in the control unit 160 into the first connection hole, a first space S1 is formed between the first cap connection housing and the first housing, and an inner volume of the first space may vary to increase or decrease by mutual screw movement between the first cap connection housing 110b and the first housing 120.

As shown in FIGS. 1, 2, 3, 4A and 4B, the central housing 130 is a hollow cylindrical member that has a female screw portion 131 formed at one open end (an upper end in the drawing) thereof to be screw-coupled to a male screw portion 127 formed on an outer surface of the first housing 120 and is assembled to enable the movement of the first housing by a screw.

Such a central housing 130 has a central partition wall 132, through which at least one communication hole 135 is formed, formed inside the body so that the central housing 130 is filled with a collected body fluid such as blood or bone marrow to centrifuge the body fluid.

Also, the central partition wall of the central housing 130 may include a locking holder portion 136 to assemble and install first and second locking bars 161, 162 of the control unit 160 in a detachable manner.

At least one O-ring member 128 for sealing a coupling site between an outer surface of the first housing 120 and an inner surface of the central housing 130 by being interposed therebetween is provided. Such an O-ring member may be selectively disposed in a ring-shaped ring groove 128a recessed from the outer surface of the first housing 120 or the inner surface of the central housing 130.

As shown in FIGS. 1, 2, 3, 4A and 4B, the second housing 140 is assembled to enable movement relative to the central housing 130 by a screw by forming a female screw portion 141 on an one open end (i.e., an inner top surface) to be screw-coupled to a male screw portion 137 formed on the other open end (i.e., an outer bottom surface in the drawing) of the central housing 130.

Such a second housing 140 has a second connection hole 145 formed in the body so that the second housing 140 is disposed to be vertically coaxial with the first connection hole 125, and the second connection hole 145 is selectively blocked or opened by the second locking bar 162 provided in the control unit 160 to open and close a connection channel.

As the second connection hole 145 is formed by a neck portion 142 extending in a tapered cross-sectional shape from an inner surface to the center of the second housing, the second housing 140 is provided in the center of the body by the neck portion 142 in a hourglass shape through which the second connection hole is formed.

Also, a plurality of reinforcing ribs may be selectively provided in a circumferential direction on an outer surface of the second housing having the neck portion 142 formed therein to reinforce the neck portion having tapering inside and outside diameters.

In this case, at least one O-ring member 138 for sealing a coupling site between an outer surface of the central housing 130 and an inner surface of the second housing 140 by being interposed therebetween is provided. Such an O-ring member may be selectively disposed in a ring-shaped ring groove 138a recessed from the outer surface of the central housing 130 or the inner surface of the second housing 140.

Accordingly, the first housing having the first connection hole and the second housing having the second connection hole are screw-coupled to both ends of the central housing, respectively. In this case, when the control unit having first and second locking bars extending in opposite directions is disposed inside the central housing to block the first and second connection holes using the first and second locking bars at the same time in order to close the connection channel, a centrifugal separation space S filled with a body fluid such as blood or bone marrow by injection is formed.

As shown in FIGS. 1, 2, 3, 4A, and 4C, the second cap connection housing 150b includes a hollow support 156 extending a predetermined length vertically from an inner surface (i.e., a bottom surface in the drawing) corresponding to the second connection hole 145, and also includes a filtering sieve for filtering a body fluid injected through a through hole 156a formed through a closed end of the hollow support.

Such a second cap connection housing 150b may include a second inner connection body 155 having a second elastic body 153 inserted and disposed in an inner hole 154 formed through the center of the body, which corresponds to the through hole, and thus may be provided as a hollow cylindrical member that is detachably assembled with the second sealing cap 150a by means of the second inner connection body 155 integrally provided with or coupled to the second cap connection housing. Like the first elastic body provided in the first cap connection housing, the second elastic body 153 has a roughly cylindrical structure in which a straight or cruciform second slit line 153a is cut in a longitudinal direction along the center of the body so that the second slit line 153a is inserted into and disposed in an inner hole 154 formed through the second inner connection body.

The inner top surface of such a second cap connection housing 150b includes a female screw portion 157 screw-coupled to a male screw portion 147 formed on an outer bottom surface of the second housing 140.

As shown in FIGS. 1, 2, 3, 4A, and 4C, the second sealing cap 150a is a roughly disk-shaped, cover-type finishing member that is detachably coupled to the second cap connection housing 150b as a second close contact body 152 is assembled to correspond to another assembly hole 151 formed through the center of the body.

The assembly hole 151 may be formed through a bottom surface of a concave groove recessed to a predetermined depth from the center of an outer surface (i.e., a bottom surface in the drawing) of the second sealing cap.

Such an inner surface (i.e., a top surface in the drawing) of the second sealing cap 150a includes a coupling portion 151a extending a predetermined length from an outer rim of the assembly hole 151 and having a female screw portion formed at an inner circumferential surface thereof.

Here, as shown in FIG. 5A, the second close contact body 152 may include an extension bar 152c having a predetermined length, which is inserted through the assembly hole 151, has a roughly disk-shaped close contact plate 152a provided at an end thereof to cover the second slit line 153a, and is gripped by a user, wherein the close contact plate 152a comes into elastic contact with the second elastic body. Also, the extension bar 152c may include a ring-shaped protruding stage 152b coming into contact with an outer rim of the assembly hole.

As shown in FIG. 5B, the second inner connection body 155 includes a coupled portion 155a having a male screw portion formed on an outer surface of one end thereof so that the male screw portion is coupled to a female screw portion of the coupling portion 151a extending a predetermined length from the outer rim of the assembly hole 151 formed in the second sealing cap 150a, and may also include a connected portion 155b formed at an outer surface of the other end thereof so that the coupled portion 155a is integrally connected to a connecting portion 156b extending a predetermined length perpendicularly from an outer rim of the through hole 156a of the hollow support 156.

In this case, the coupling between the coupled portion 155a of the second inner connection body 155 and the coupling portion 151a of the second sealing cap 150a is shown and described as the coupled portion 155a and the coupling portion 151a being detachably assembled by a screw-coupling method, but the present invention is not limited thereto. For example, the coupled portion 155a and the coupling portion 151a may be detachably assembled by other coupling methods.

Also, the connected portion 155b of the second inner connection body 155 may be integrally provided with the second cap connection housing by an ultrasonic welding method using welding heat of ultrasonic waves intensively applied to a contact site in a state in which the connected portion 155b is put on the connecting portion 156b formed at the hollow support 156 so that the connected portion 155b comes into contact with the connecting portion 156b, but the present invention is not limited thereto. For example, the connected portion and the connecting portion may be coupled to each other by a screw coupling method or a bonding method.

In this case, the connecting portion 156b of the hollow support 156, with which the connected portion 155b of the second inner connection body 155 comes contact in a state in which the connected portion 155b is put on the connecting portion 156b, may include a ring-shaped anchoring groove to increase a contact area with inner and outer rims of the connected portion 155b and stably and uniformly come into contact with the inner and outer rims of the connected portion 155b.

Also, when the connected portion of the second inner connection body 155 is provided as a stand-alone structure which is coupled to the connecting portion formed at the hollow support by means of any one of ultrasonic welding, screw coupling, and bonding methods, a primary assembly process of inserting the second elastic body 153 into the inner hole 154 of the second inner connection body 155 having a stand-alone structure is first performed, and a secondary assembly process of integrally coupling the second inner connection body to a connecting portion of the hollow support is then performed.

On the other hand, when the second inner connection body 155 is provided as an integral structure extending from the connecting portion 156b formed at the hollow support, the number of component parts may be reduced by excluding an assembly process of integrally connecting the connected portion of the second inner connection body and the connecting portion of the hollow support to each other.

Accordingly, when the second sealing cap having the first close contact body is coupled to the second cap connection housing by means of the second inner connection body, the second close contact body composed of a soft elastic material such as a rubber material comes into elastic contact with a second slit line, which forms a connection channel into which an inlet of a syringe is forcibly inserted, to seal the second slit line, thereby safely preventing the contents from flowing out through the second slit line during centrifugation. On the other hand, the inlet of the syringe may be forcibly inserted during separation of the second sealing cap to expose the second slit line forming a connection channel to the outside and basically prevent external air from flowing in during injection of the body fluid at the same time.

Also, the filtering sieve 159 serves to filter foreign substances included in a body fluid flowing in a second space S2 formed between the second housing 140 and the second cap connection housing 150b through a through hole 156a, which communicates with the second slit line into which the inlet of the syringe is forcibly inserted during the separation of the second sealing cap 150a.

In this case, when the body fluid is bone marrow, the foreign substances filtered through the filtering sieve may be bone fragments included during collection of bone marrow.

Such a filtering sieve 159 may include a roughly hemispherical sieve having a flange portion formed at an outer rim thereof, wherein the flange portion is bonded and fixed onto an outer surface of the hollow support, which has the through hole 156a formed therein, by means of a binder such as a bonding agent.

A fixing plate 159a for fixing and installing the filtering sieve in a hollow support through another through hole corresponding to the through hole may be included between the filtering sieve 159 and the hollow support 156.

Figure 6A:
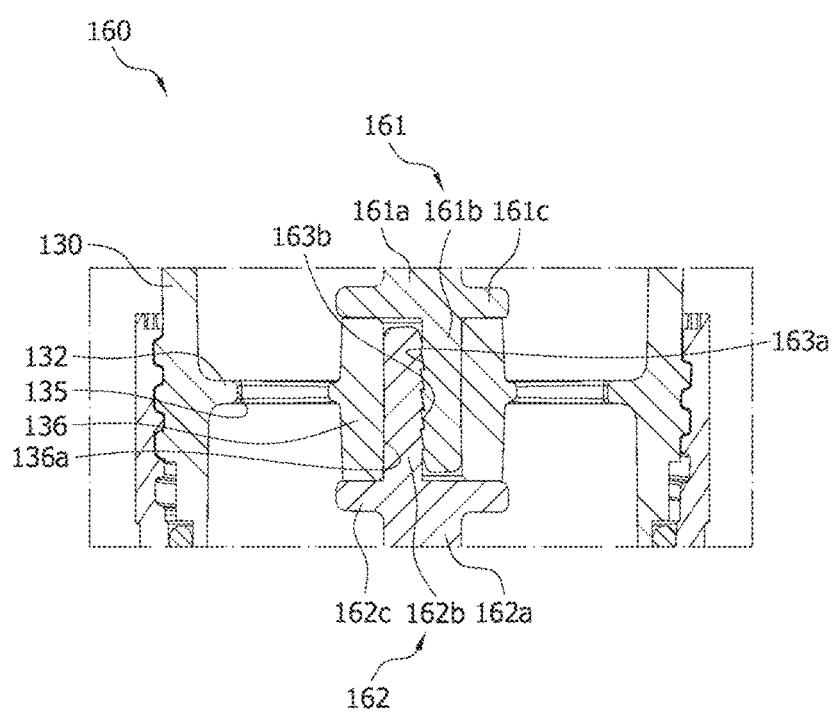
FIGS. 6A and 6B are detail views showing a control unit applied to an apparatus for separating a body fluid according to an embodiment of the present invention.
Figure 6B:
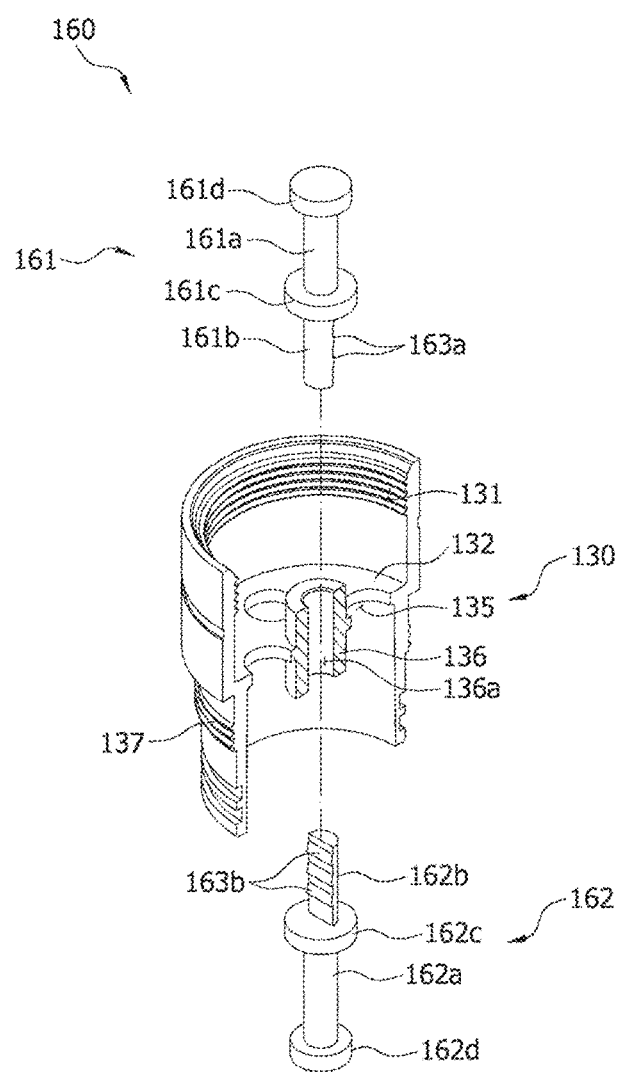

As shown in FIGS. 6A and 6B, the control unit 160 includes a first locking bar 161 extending a predetermined length from the central partition wall 132 provided in the central housing 130 toward the first connection hole 125, and a second locking bar 162 extending a predetermined length toward the second connection hole 145 to selectively block or open the first connection hole or the second connection hole, which move in opposite directions relative to the central partition wall, during mutual movement between the first and second housings and the central housing.

Such first and second locking bars 161, 162 serve to form a first space S1 between the first sealing cap 110 and the first housing 120, or form a second space S2 between the second sealing cap 150 and the second housing 140 by selectively blocking or opening the first and second connection holes when the first and second housings move relative to the central housing, and serve to selectively communicate between the first and second spaces according to a centrifugation process or block the connection channel while forming a centrifugal separation space S in an inner space of the central housing, which corresponds to a space between the first and second spaces.

Also, the central partition wall 132 of the central housing 130 may include a locking holder portion 136 to assemble and install the first and second locking bars 161, 162 in a fixing hole 136a by inserting respective ends of the first and second locking bars in order to correspondingly insert the respective ends of the first and second locking bars 161, 162 to vertically position and fix the first and second locking bars relative to the horizontal central partition wall.

As shown in FIGS. 6A and 6B, the first and second locking bars 161, 162 may have first and second insertion bars 161a, 162a inserted to correspond to the ends of the first and second connection holes 125, 145, respectively, and may include first and second fixing bars 161b, 162b extending a predetermined length from the other ends of the first and second insertion bars, respectively, to be detachably assembled to correspond to the fixing hole 136a of the locking holder portion 136, respectively.

Ring-shaped first and second protruding stages 161c, 162c are formed at boundary regions between the first and second insertion bars 161a, 162a and the first and second fixing bars 161b, 162b, respectively, to control insertion depths of the first and second fixing bars while being in contact with and caught in the fixing hole 136a of the locking holder portion.

The ring-shaped first and second protruding stages 161c, 162c are shown and described as being integrally provided at boundary regions between the first and second insertion bars and the first and second fixing bars in the middle of lengths of the first and second locking bars, but the present invention is not limited thereto. For example, the ring-shaped first and second protruding stages 161c, 162c may include a ring-shaped member having a female screw portion screw-coupled to a male screw portion formed in the middle of the lengths of the first and second locking bars.

Also, the first and second fixing bars 161b, 162b may include planar portions whose bodies are partially cut off to face each other in order to be joined in the same cross-sectional shape as a cross-sectional shape of the fixing hole while being assembled to correspond respectively to the fixing hole 136a of the locking holder portion 136 to overlap each other.

In this case, when the fixing hole is in the form of a circular hole, the first and second fixing bars are formed in a semicircular cross-sectional shape, respectively, to be joined in the form of a circular bar and inserted and fixed in the fixing hole, but the present invention is not limited thereto. For example, the cross-sectional shapes of the first and second fixing bars may vary according to the shape of the fixing hole.

In the first and second fixing bars, one lateral planar portion of the pair of planar portions facing each other may include a plurality of latching portions 163a formed to protrude at predetermined intervals, and the other planar portion may include latched portions 163b latched with the latching portions to generate a latching force.

Here, the latching portions 163a and the latched portions 163b may be formed as protruding stages having tapered cross-sectional shapes facing each other, or may be provided as latching stages or provided as latching grooves formed in a recessed shaped and latching stages latched with the latching grooves.

In this case, it is desirable to prevent a slipping phenomenon between the facing planar portions of the first and second fixing bars overlapped and joined in the fixing hole of the locking holder portion by disposing the latching portions between the adjacent latched portions to generate a latching force.

Accordingly, the first and second fixing bars 161b, 162b that are separately inserted into the fixing hole of the locking holder portion 136 to overlap each other serve to extend the total lengths of the first and second locking bars or return to their original states by adjusting an insertion depth in the fixing hole to change latching positions between the latching portions and the latched portions.

Also, insertion portions 161d, 162d having an outside diameter relatively larger than an outside diameter of the first and second fixing bars 161b, 162b may be formed at ends of the first and second locking bars, respectively, so that the insertion portions 161d, 162d can be inserted to correspond to the first and second connection holes.

A process of centrifuging a centrifugate (e.g., a body fluid such as marrow or blood) twice using the kit 100 for separating and concentrating body fluid cells having the aforementioned configuration according to the embodiment will be described.

Figure 7A:
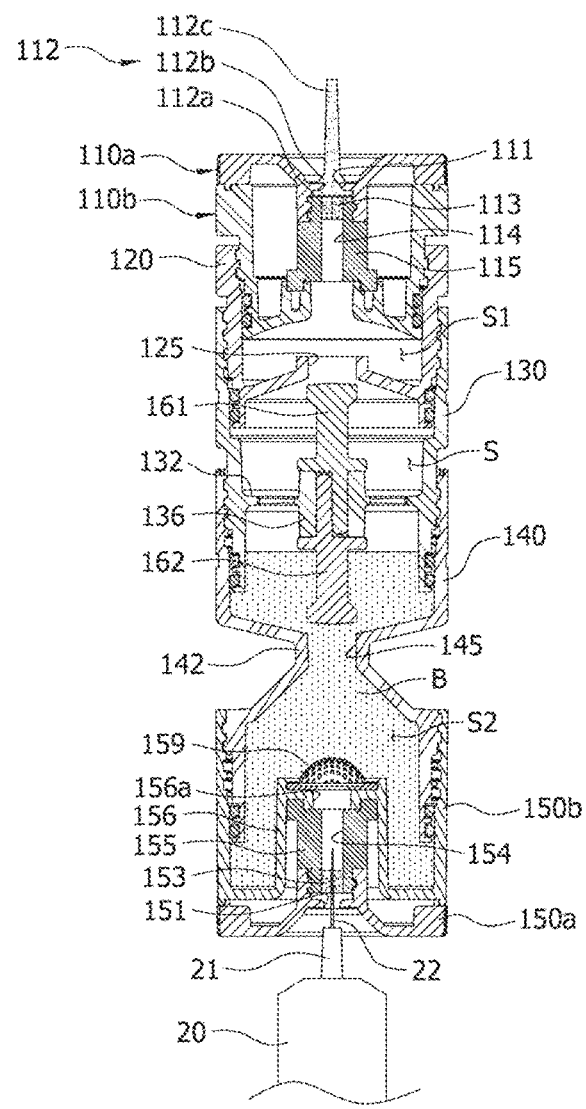
FIGS. 7A to 7F are use state views showing an apparatus for separating a body fluid according to a first embodiment of the present invention.

First of all, as shown in FIG. 7A, when the second close contact body 152 is not assembled in the assembly hole of the second sealing cap in a state in which the first connection hole 125 of the first housing 120 and the second connection hole 145 of the second housing 140 are opened, and the second cap connection housing 150b and the second sealing cap 150a are coupled, the second slit line of the second elastic body press-fitted to be assembled with the second inner connection body through the assembly hole 151 is exposed to the outside.

In this state, when an inlet 21 of a syringe 20 from which an injection needle is removed, or an injection needle 22 is forcibly inserted through the second slit line exposed to the outside, the inlet of the syringe 20 or the injection needle is connected to communicate with the inner hole of the second inner connection body through the second slit line of the second elastic body formed of an elastic body such as a rubber material.

Next, the body fluid B such as blood or bone marrow injected by a pressure applied by a piston operation of the syringe 20 is injected through the hemispherical filtering sieve 159 facing the through hole 156a of the hollow support 156 in which the second inner connection body is disposed.

In this case, the inlet of the syringe 20 or the injection needle is press-fitted to be in close contact with the second slit line of the second elastic body by an elastic force of the second elastic body to basically prevent external air from coming into contact with a body fluid or being mixed during a process of injecting the body fluid.

At the same time, the foreign substances such as bone fragments included in the body fluid are removed during a process of passing through the filtering sieve 159, and only the filtrated body fluid is injected into a centrifugal separation space so that the centrifugal separation space is filled with a predetermined amount of the body fluid.

Figure 7B:
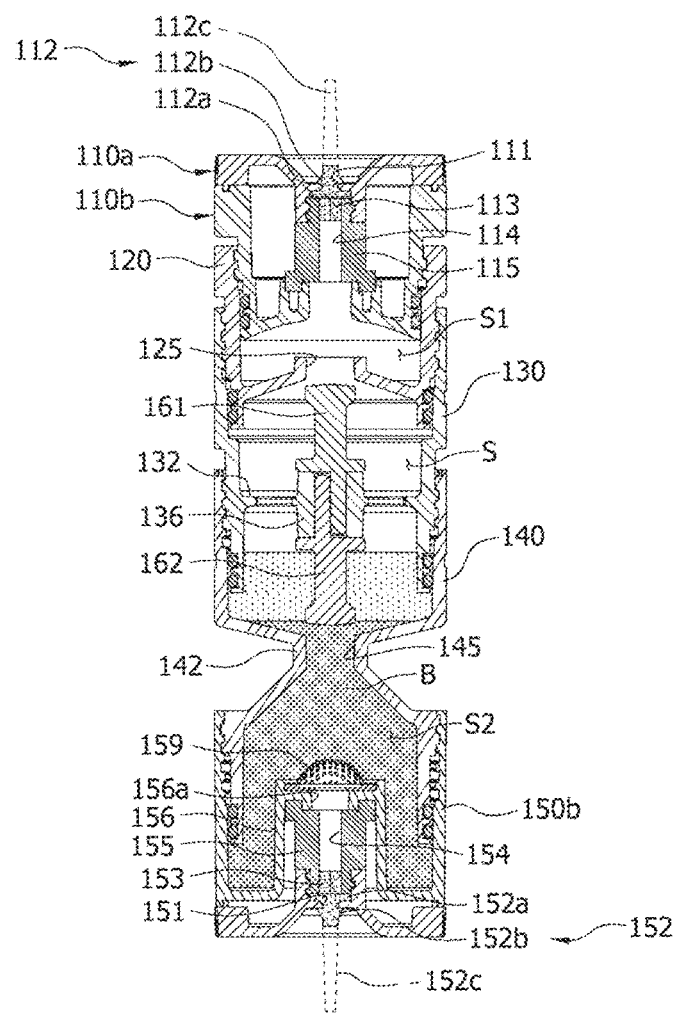

Subsequently, after an operation of injecting a body fluid using the syringe is completed, as shown in FIG. 7B, when the close contact plate 152a of the second close contact body 152 is press-fitted through the assembly hole 151 in a state in which the syringe is disconnected and removed, the close contact plate of the second close contact body is elastically brought into contact with and brought into close contact with an end of the second elastic body 153 having the second slit line formed therein. Therefore, the second slit line 153a forming an injection channel is sealed by the close contact between the second close contact body and the second elastic body composed of an elastic material.

In this case, the close contact plate of the first close contact body is brought into close contact with an end of the first elastic body 113 having the first slit line formed therein to seal the first elastic body 113 by press-fitting the close contact plate 112a of the first close contact body 112 into the assembly hole 111 of the first sealing cap 110a of the assembly hole 111 through the assembly hole 111 before performing a primary centrifugation process in a centrifuge.

Each of the extension bars 112c, 152c of the first and second close contact bodies 112, 152 is preferably cut and removed before performing a primary centrifugation process so that there is no interference with other members in the centrifuge in which the centrifugation process is performed.

Then, a process of primarily centrifuging the body fluid B is performed using a centrifuge in a state in which the second connection hole 145 of the second housing is opened so that the centrifugal separation space S and the second space S2 communicate with each other, and the assembly holes of the first and second sealing caps are closed by the first and second close contact bodies, respectively.

Figure 7C:
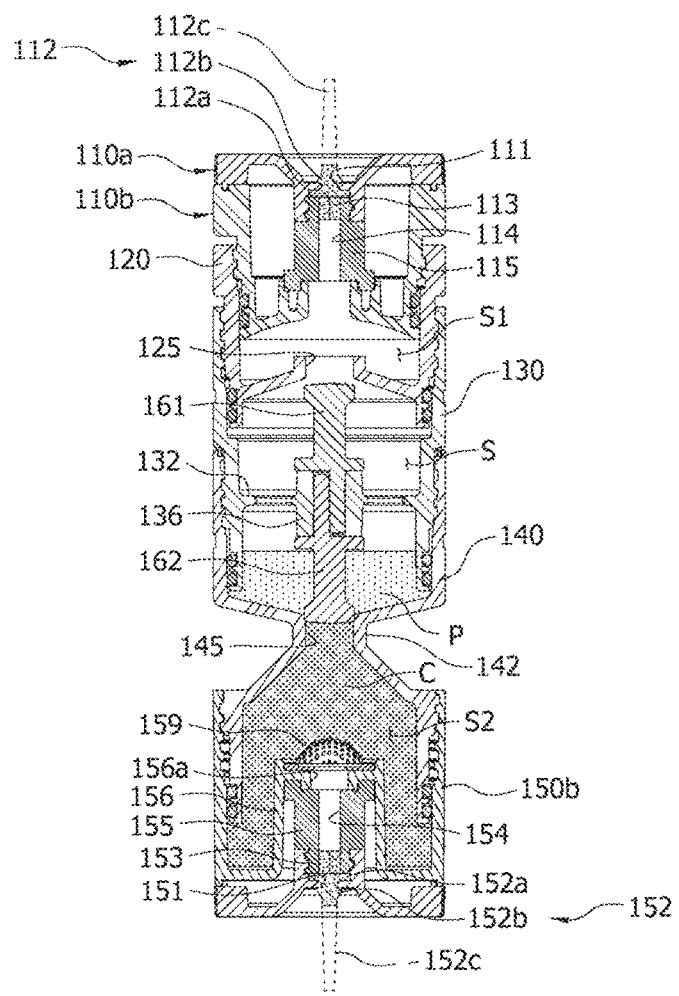

When the primary centrifugation is completed, the blood cell component C and the plasma component P included in the centrifuged body fluid B such as bone marrow are separated in a vertical direction due to the specific gravity difference, as shown in FIG. 7C. In this case, a boundary layer between the blood cell component C and the plasma component P, which are separated and stacked in the vertical direction due to the specific gravity difference is formed in the second connection hole 145 or formed at an upper or lower side of the second connection hole 145, depending on the amount of the body fluid to be centrifuged.

In this case, separation layers constituted by the primarily centrifuged blood cell component and plasma component are visually identified by colors exposed to the outside since the first and second housings and hollow housings are formed of a transparent material.

In this state, an operator delicately manually adjusts a position of the second cap connection housing relative to the second housing by moving the second cap connection housing 150b, by moving a screw, to some extent relative to the second housing 140 in a forward or reverse direction to dispose a boundary layer between the blood cell component C and the plasma component P in the middle or lower end of the second connection hole 145.

Then, when the second housing is rotated relative to the central housing in a forward or reverse direction to close the second connection hole 145 with the second insertion bar of the second locking bar, only the blood cell component serving as the centrifugate is separated to remain in a second space S2 formed between the second housing and the second cap connection housing.

Therefore, the centrifuged blood cell component is removed together with the foreign substances filtered through the hemispherical filtering sieve during an operation of disassembling the second cap connection housing coupled to the second housing, and the disassembled second cap connection housing is re-assembled into the second housing.

Figure 7D:
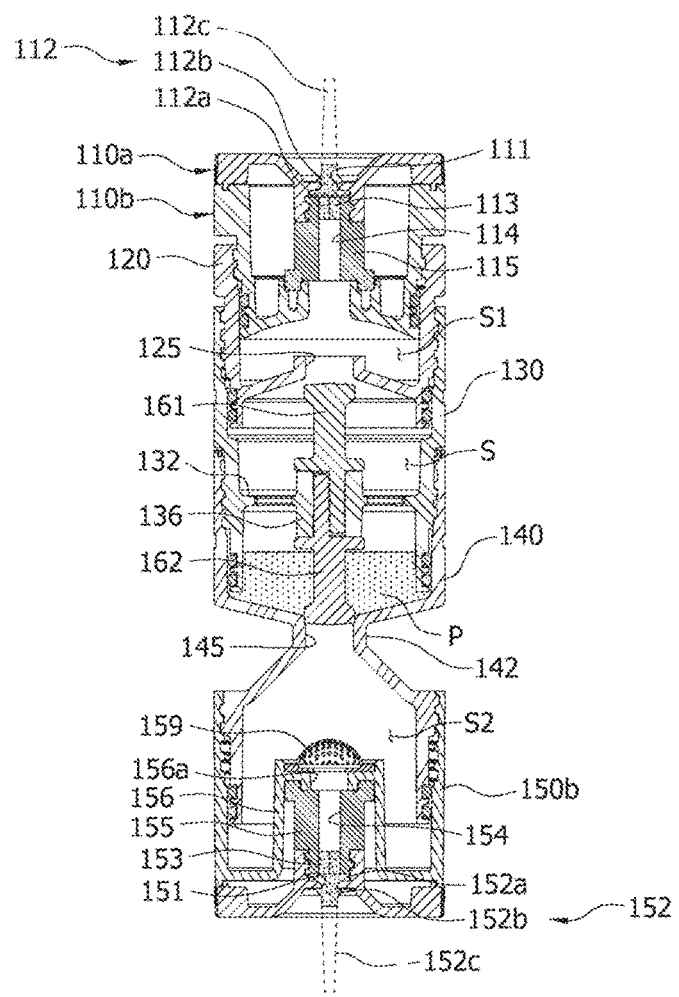

Accordingly, as shown in FIG. 7D, only the plasma component P remains in the centrifugal separation space S of the central housing, and the second space S2 is emptied as the blood cell component C is separated and removed.

Figure 7E:
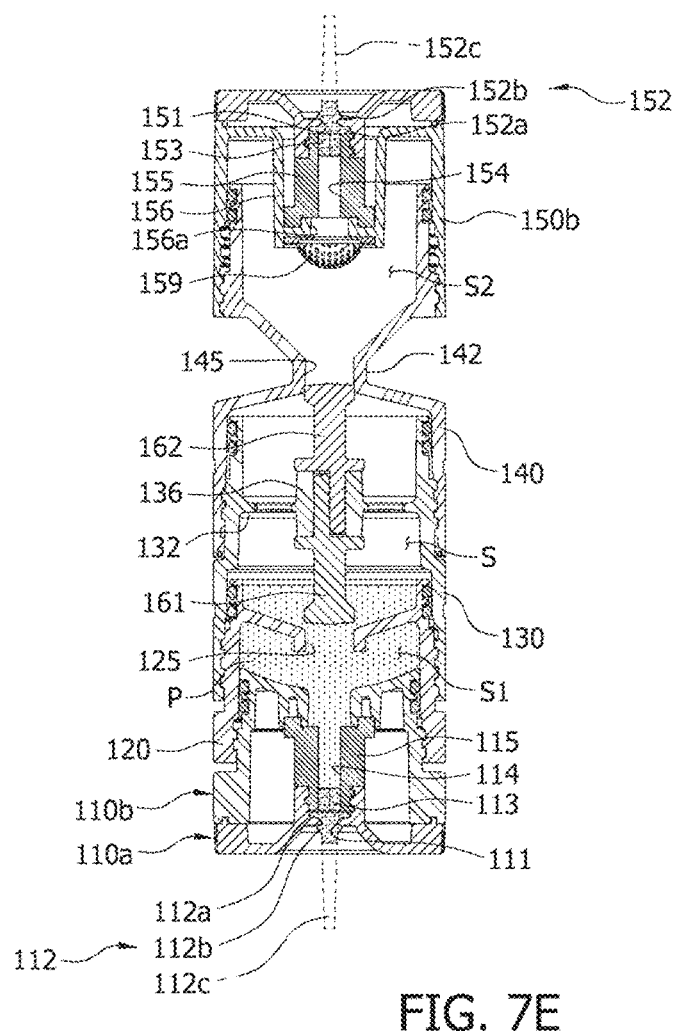

Then, as shown in FIG. 7E, when the first sealing cap and the first cap connection housing 110b used as lower members, and the second sealing cap and the second cap connection housing used as upper members are reversed at an angle of 180°, the primarily centrifuged plasma component P is allowed to move to the first space S1 through the opened first connection hole 125.

In this case, the total volume of the secondary centrifugate such as plasma component P may be the same as or different from the total volume of the first space S1, an operator may secondarily centrifuge the plasma component P by rotating the first cap connection housing, and properly adjusting (i.e., increasing or decreasing) the total volume of the first space so that the separated boundary layer is positioned in the first connection hole.

Also, an operation of regulation through this rotation of the first cap connection housing may be performed to regulate a degree of enrichment of a PRP layer as the final product.

Subsequently, when a secondary centrifugation process is performed on the plasma component P in the centrifuge, the secondarily centrifuged plasma component P is vertically separated into a PRP layer P1 as platelet-rich plasma and a PPP layer P2 as platelet-poor plasma due to the specific gravity difference, and a separated boundary layer between the centrifuged PRP layer P1 and the PPP layer P2 may be formed in the first connection hole or formed at an upper or lower side of the first connection hole, depending on the amount of the plasma component to be centrifuged.

In this case, the secondarily centrifuged PRP layer P1 (as the platelet-rich plasma) and PPP layer P2 (as the platelet-poor plasma) may be distinguished and identified with the naked eye through the first and second housings and the hollow cylindrical housing made of a transparent material.

Figure 7F:
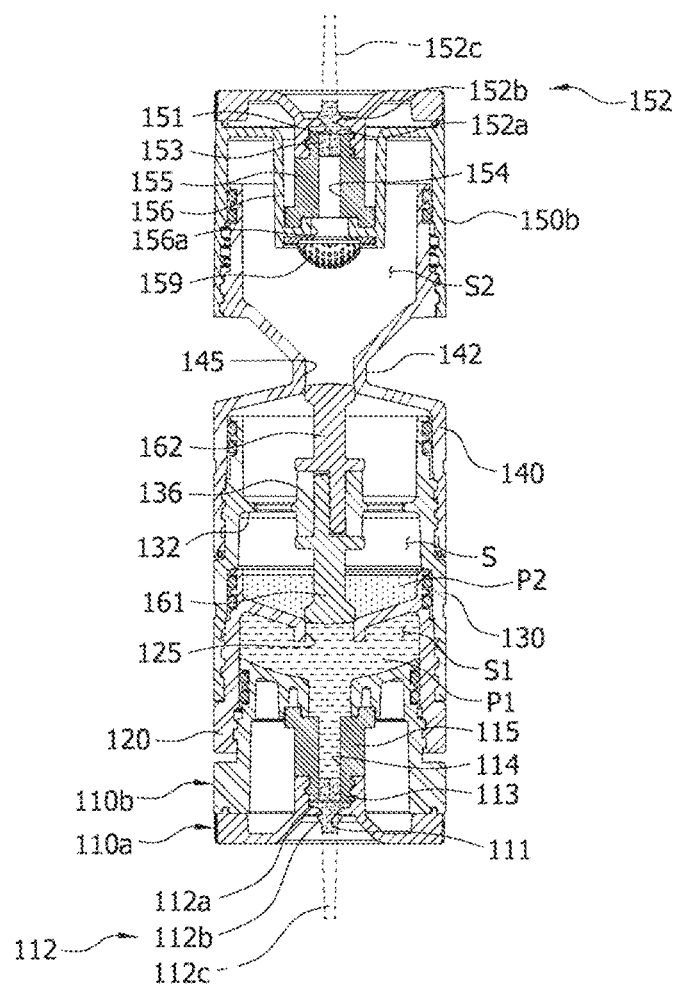

Subsequently, as shown in FIG. 7F, because a position of the first cap connection housing relative to the first housing 120 may be manually adjusted so that the separated boundary layer between the PRP layer P1 and the PPP layer P2 is positioned in the middle or lower end of the first connection hole 125 by moving the first cap connection housing 110*b*, by moving a screw, to some extent in a forward or reverse direction, the PPP layer P2 is disposed as an upper layer in the centrifugal separation space S, and the PRP layer P1 is disposed as a lower layer in the first space S1.

In this state, when the first housing is rotated relative to the central housing to close the first connection hole 125 with the first locking bar, only the PRP layer P1 may be isolated so that the PRP layer P1 remains as the centrifugate in the first space S1, and may be secondarily separated.

When the first close contact body assembled in the assembly hole of the first sealing cap 110*a* is separated and removed from the PRP layer P1 serving as the final centrifugate, the PRP layer P1, the second slit line of the first elastic body is exposed to the outside through the assembly hole.

In this state, the inlet of the syringe or the injection needle is forcibly inserted through the first slit line to extract the whole amount of the secondarily separated PRP layer P1 from the first inner connection body and collect the extracted PRP layer P1 without any contact with external air. As a result, the operation of centrifuging a body fluid is completed.

According to the embodiments of the present invention as described above, the kit has the following effects.

When a body fluid such as blood or bone marrow collected using a syringe is injected and fed into a centrifugal separation space, or during an operation of extracting the final centrifuged product from the centrifugal separation space, the contamination of the centrifugate (e.g., a body fluid) or the contamination of the final product (e.g., PRP) may be prevented by basically preventing the inflow of external air and basically preventing the contact with external air, resulting in improved reliability.

Although the present invention has been shown and described with reference to the aforementioned embodiments and the accompanying drawings, it will be understood by persons having ordinary skill in the art to present invention belongs that various substitutions, changes and modifications may be made therein without departing from the spirit and scope of the present invention.

BRIEF DESCRIPTION OF PARTS IN THE DRAWINGS

110*a*: first sealing cap
110*b*: first cap connection housing
112, 152: first and second close contact bodies
113, 153: first and second elastic bodies
113*a*, 153*a*: first and second slit lines
115, 155: first and second inner connection bodies
120: first housing
130: central housing
140: second housing
150*a*: second sealing cap
150*b*: second cap connection housing
156: hollow support
159: filtering sieve
160: control unit
161, 162: first and second locking bars S: centrifugal separation space
S1: first space
S2: second space

What is claimed is:

1. A kit for separating and concentrating body fluid cells, comprising:
   a first sealing cap provided with a first close contact body in an assembly hole formed through a body;
   a first cap connection housing having a first inner connection body in which a first elastic body having a first slit line formed at an end thereof, with which the first close contact body comes into elastic contact when coupled to the first sealing cap, is inserted and disposed in an inner hole so that the first inner connection body is assembled with the first sealing cap;
   a first housing having one end screw-coupled to the first cap connection housing and having an inner partition wall formed therein so that a first connection hole corresponding to the inner hole is formed through the inner partition wall;
   a central housing having one end screw-coupled to the other end of the first housing so that the one end of the central housing and the other end of the first housing are movable relative to each other by a screw and having a central partition wall, through which at least one communication hole is formed, formed therein to be filled with a body fluid;
   a second housing having one end screw-coupled to the other end of the central housing so that the one end of the second housing and the other end of the central housing are movable relative to each other by a screw and having a second connection hole, which corresponds to the first connection hole, formed therein;
   a second cap connection housing having a hollow support extending vertically from an inner surface thereof, which corresponds to the second connection hole, a filtering sieve for filtering a body fluid injected through a through hole formed in the hollow support, and a second inner connection body in which a second elastic body is inserted and disposed in an inner hole corresponding to the through hole so that the second cap connection housing is screw-coupled to the other end of the second housing;
   a second sealing cap having a second close contact body coming into elastic contact with an end of the second elastic body having a second slit line formed therein when coupled to the second cap connection housing so that the second close contact body is coupled to the second inner connection body; and
   a control unit having a first locking bar extending from the central partition wall toward the first connection hole, and a second locking bar extending from the central partition wall toward the second connection hole to selectively block or open the first connection hole or the second connection hole during mutual movement between the first and second housings and the central housing.

2. The kit of claim 1, wherein the first close contact body or the second close contact body comprises an extension bar having a predetermined length, which is inserted through an assembly hole of the first sealing cap or an assembly hole of the second sealing cap and has a close contact plate provided at an end thereof to cover the first slit line or the second slit line, wherein the close contact plate comes into elastic contact with the first elastic body or the second elastic body.

3. The kit of claim 2, wherein the extension bar comprises a ring-shaped protruding stage coming into contact with an outer rim of the assembly hole of the first sealing cap or the assembly hole of the second sealing cap.

4. The kit of claim 1, wherein the first inner connection body comprises a coupled portion coupled to a coupling portion extending from an outer rim of the assembly hole formed in the first sealing cap, and a connected portion integrally connected to a connecting portion extending from an outer rim of the central hole formed in the inner partition wall of the first cap connection housing.

5. The kit of claim 4, wherein the first inner connection body is provided as a stand-alone structure whose portion with which the connecting portion of the first cap connection housing comes into contact is coupled to the connected portion by means of any one of ultrasonic welding, screw coupling, and bonding methods.

6. The kit of claim 4, wherein the connecting portion of the first cap connection housing comprises a ring-shaped anchoring groove coming into contact with the connected portion of the first inner connection body.

7. The kit of claim 4, wherein the first inner connection body is provided as an integral structure extending from the connecting portion formed on the inner partition wall of the first cap connection housing.

8. The kit of claim 1, wherein the second inner connection body comprises a coupled portion coupled to a coupling portion extending from an outer rim of the assembly hole formed in the second sealing cap, and a connected portion integrally connected to a connecting portion extending from an outer rim of the through hole formed in the hollow support.

9. The kit of claim 8, wherein the second inner connection body is provided as a stand-alone structure whose portion with which the connecting portion of the hollow support comes into contact is coupled to the connected portion by means of any one of ultrasonic welding, screw coupling, and bonding methods.

10. The kit of claim 8, wherein the connecting portion of the hollow support comprises a ring-shaped anchoring groove coming into contact with the connected portion of the second inner connection body.

11. The kit of claim 8, wherein the second inner connection body is provided as an integral structure extending from the connecting portion formed at the hollow support.

12. The kit of claim 1, wherein the first and second locking bars comprise first and second insertion bars inserted into the first and second connection holes so that ends of the first and second insertion bars correspond, respectively, to the first and second connection holes, and first and second fixing bars assembled to correspond to fixing hole of a locking holder portion formed at the central partition wall, respectively.

13. The kit of claim 12, wherein the first and second locking bars comprise ring-shaped first and second protruding stages formed at boundary regions between the first and second insertion bars and first and second fixing bars, respectively, to be in contact with and caught in the fixing hole of the locking holder portion.

14. The kit of claim 12, wherein the first and second fixing bars comprise a pair of planar portions whose bodies are partially cut off to face each other in order to be joined in the same cross-sectional shape as a cross-sectional shape of the fixing hole while being assembled to correspond respectively to the fixing hole of the locking holder portion to overlap each other.

15. The kit of claim 14, wherein one lateral planar portion of the pair of planar portions comprises a plurality of latching portions formed to protrude at predetermined intervals, and the other planar portion comprises a plurality of latched portions latched with the latching portions to generate a latching force.

* * * * *